United States Patent [19]
Hansen et al.

[11] Patent Number: 5,693,027
[45] Date of Patent: Dec. 2, 1997

[54] ADAPTOR TOP

[75] Inventors: Ib Hansen, Herlev; Søren Mikkelsen, Holte; Frits Frydendal Bonnichsen, Lynge, all of Denmark

[73] Assignee: Novo Nordisk A/S, Bagsvaerd, Denmark

[21] Appl. No.: 313,651

[22] Filed: Sep. 26, 1994

Related U.S. Application Data

[63] Continuation of Ser. No. 53,503, Apr. 27, 1993, abandoned, which is a continuation of Ser. No. 768,684, filed as PCT/DK91/00282, Sep. 20, 1991, published as WO92/04926, Apr. 2, 1992, abandoned.

[30] Foreign Application Priority Data

Sep. 21, 1990 [DK] Denmark ................................. 2282/90
May 16, 1991 [DK] Denmark ................................. 926/91

[51] Int. Cl.$^6$ .................................................. A61M 5/00
[52] U.S. Cl. ........................... 604/232; 604/200; 604/51
[58] Field of Search ........................... 604/232, 240–242, 604/200, 201, 905, 415, 181, 51; 215/324, DIG. 3

[56] References Cited

U.S. PATENT DOCUMENTS

| | | | |
|---|---|---|---|
| Re. 31,873 | 4/1985 | Howes | 128/674 |
| 31,873 | 4/1861 | Howes | 128/674 |
| Re. 31,878 | 5/1985 | Howes | 128/674 |
| 1,594,493 | 8/1926 | Brown | 604/232 |
| 2,020,828 | 11/1935 | Goldberg | 604/201 |
| 2,818,864 | 1/1958 | Hudson | 604/415 |
| 2,865,372 | 12/1958 | Miskel et al. . | |
| 3,130,724 | 4/1964 | Higgins et al. | 604/201 |
| 3,130,742 | 4/1964 | Higgins et al. | 604/201 |
| 3,336,924 | 8/1967 | Sarnoff et al. | 604/415 |
| 3,375,825 | 4/1968 | Keller | 604/201 |
| 3,820,652 | 6/1974 | Thackston | 604/201 X |
| 3,895,633 | 7/1975 | Bertner et al. | 604/232 X |
| 3,916,893 | 11/1975 | De Felice . | |
| 3,989,044 | 11/1976 | Meierhoefer | 604/243 X |
| 4,089,432 | 5/1978 | Crankshaw et al. | 604/415 X |
| 4,490,142 | 12/1984 | Silvern | 604/241 |
| 4,664,656 | 5/1987 | Taddei | 604/241 |
| 4,740,205 | 4/1988 | Seltzer | 604/192 |
| 4,768,568 | 9/1988 | Fournier et al. | 604/905 X |
| 4,781,701 | 11/1988 | Geprägs | 604/240 |
| 4,944,736 | 7/1990 | Holtz | 604/403 |
| 4,948,000 | 8/1990 | Grobenkort | 215/DIG. 3 X |
| 5,205,833 | 4/1993 | Harsh et al. | 604/240 |

FOREIGN PATENT DOCUMENTS

| | | |
|---|---|---|
| 2 137 405 | 2/1973 | Germany . |
| 0315980 | 10/1969 | Switzerland .......................... 604/201 |
| 0501411 | 2/1971 | Switzerland . |
| 501 411 | 2/1971 | Switzerland . |
| 1205021 | 9/1970 | United Kingdom ................... 604/200 |
| 1 437 595 | 5/1976 | United Kingdom . |
| 1 525 455 | 9/1978 | United Kingdom . |
| WO 89/02760 | 4/1989 | WIPO . |

*Primary Examiner*—Michael Powell Buiz
*Assistant Examiner*—A. T. Nguyen
*Attorney, Agent, or Firm*—Steve T. Zelson, Esq.; James J. Harrington, Esq.

[57] ABSTRACT

A plastic top for adapting to a chosen syringe (14) a standard cartridge (8) of the kind having a neck (9) with a flange (10) and being closed by a rubber membrane (11) sealingly secured against the flange (10) by a metal cover (12) having its edge beaded behind the flange. This plastic top has a bore (2) for receiving the neck part (9) of the cartridge (8), which bore (2) has a diameter making it fit over the metal cover (12) and is provided with protrusions (3;9) gripping behind the edge of the metal cover (12) when the neck part (9) is inserted in the bore. The outer contour of the plastic top is adapted to the syringe type in which the cartridge is going to be used.

The plastic top is provided with a thread (5;18) coaxial with the bore to receive a needle hub (13) in a way making its needle (15) penetrate the membrane (11) of the cartridge (8) when the hub (13) is mounted on the thread (5) of the plastic top.

19 Claims, 3 Drawing Sheets

1

ADAPTOR TOP

This application is a continuation application of co-pending application Ser. No. 08/053,503, filed on Apr. 27, 1993, abandoned, which is a continuation of application Ser. No. 07/768,684 filed as PCT/DK91/00282 Sep. 20, 1991 published as WO92/04926 Apr. 2, 1992, the contents of which are incorporated herein by reference now abandoned.

The invention relates to ampules for pen syringes. Such ampoules are commonly shaped as a glass tube being at one end closed by a piston, which may be pressed into the tube to expel the content of the tube at the other end of the tube. This other end is formed as a bottle neck, the outer end of which is closed by a rubber membrane, which may be pierced by an injection needle through which the content is expelled.

DESCRIPTION OF THE RELATED ART

In a standard cartridge the outer end of the bottleneck is provided with an external flange supporting the rubber membrane, and this membrane is sealingly secured over the opening of the neck against the flange by a metal cap having a central opening exposing the central part of the membrane over the opening of the neck, having side walls extending along the sides of the membrane and the flange, and having its end beaded to grip under the lower side of the flange.

As new types of pen syringes were developed the cartridges or at least the neck thereof was given different shapes to accommodate these types of syringes. The use of plastic closures instead of the standard metal cap has made it necessary to design the flanges for cooperation with such plastic tops which demand a greater accuracy of the glass flange if a reliable sealing shall be obtained. Consequently, the different insulin types each have to be marketed in different types of cartridges whereby the manufacturing and the stockpiling is made complicated.

SUMMARY OF THE INVENTION

It is the object of the invention to provide a system of tops making a standard cartridge usable in an optional pen.

This is obtained by a plastic top which according to the invention has a bore for receiving the neck part of the cartridge, the bore having a diameter fitting over the metal cover, the inner wall of the bore being provided with protrusions for gripping behind the edge of the metal cover when the neck part is inserted into the bore, and the outer contour of the top being formed to adapt the chosen syringe type.

By using such a plastic top only one type of cartridges has to be manufactured as the adaption to a chosen type of syringe is made by the choice of plastic top. This means that the department filling the cartridges will not have to dispose of different filling machines or to rearrange existing machines to fill different types of cartridges with the same type of medicine. The mounting of the plastic top need not take place under sterile conditions as do the filling, and as the plastic top is of no importance to the sealing of the cartridges, the high accuracy demand may be reduced as the protrusions in the bore only have to secure the plastic top so that it cannot easily be removed, but do not have to prevent rotation or small axial movements of the plastic top on the neck part.

According to the invention the plastic top may be provided with a thread coaxial with the bore to receive a threaded needle hub carrying a double pointed needle, the thread of the top being provided so that when the needle hub is screwed onto the top mounted on a cartridge the one pointed end of the needle will penetrate the rubber membrane of the cartridge. This way the plastic top may serve the same purpose as do the known plastic closures.

The plastic top may be provided with means for keyed engagement with corresponding means in a syringe to keep it unrotable when mounted with a cartridge in the syringe. This is of importance when a needle should be screwed onto the top. In some types of syringes such keyed engagement between cartridge and syringe is further used to ensure that only a certain type of cartridge is used in the syringe.

According to the invention the top may be made from a coloured plastic in accordance with a colour code system for the content of the cartridges. Such a colour code system exists for insulin preparations revealing if a cartridge contains slow or quick acting insulin or a mixture thereof. Especially where the code top having an external thread is used the user is reminded of the type of medicine in the cartridge each time he has to screw a new needle onto the thread of the plastic top.

The plastic top may surround only the neck part of the cartridge or it may cover a bigger or smaller part of the cartridge and even form a part of the housing of a syringe, which may simplify the changing of cartridges.

BRIEF DESCRIPTION OF THE DRAWINGS

The invention will now be described in further details with reference to the drawing, wherein.

DESCRIPTION OF THE PREFERRED EMBODIMENTS

Figure 1:
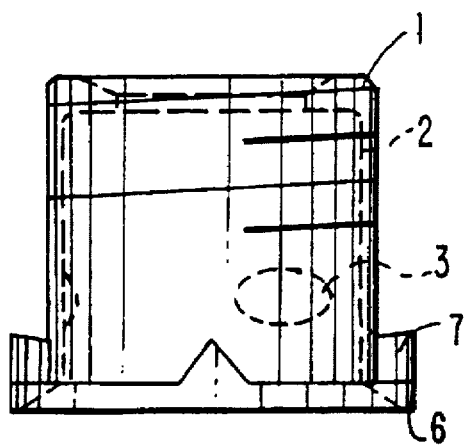
FIG. 1 shows a front view of an embodiment of an adaptor top according to the invention.

An adaptor top shown in FIG. 1 comprises a body 1 with a bore having a diameter slightly bigger than the diameter of the metal cap of a standard cylinder ampoule. The cylindric inner wall 2 of the bore is provided with protrusions 3 which may grip under the beaded lower edge of the metal cap of a standard ampoule, when the top is fitted with its bore over the closure of the ampoule. In the shown embodiment there are three protrusions with an angular spacing of 120°, but more protrusions or a single ring shaped protrusion may be used just as the scope of the invention is not deviated from by using two or one protrusion.

The protrusions 3 are given a height ensuring a good grip under the edge of the metal cap and the top is mounted by pressing the top with its bore over the metal cap making the protrusion pass the cap by the plastic material of the top being incidentally deformed. The protrusions 3 are placed in the bore of the body 1 in a position making them reach their gripping position under the edge of the metal cap before the insertion of the ampoule neck part into the bore is stopped by the top of the closure abutting the bottom of the bore or the lower edge of the body 1 abutting the ampoule around its neck.

At the bottom of its bore 2 the adaptor top is provided with an opening 4 exposing part of the top of the metal cap with the rubber membrane laid bare. The adaptor top in the shown embodiment is intended for a needle in a hub having an internal thread and consequently it is provided with an outer thread 5 for receiving such a hub with its needle projecting through the opening 4.

Figure 6:
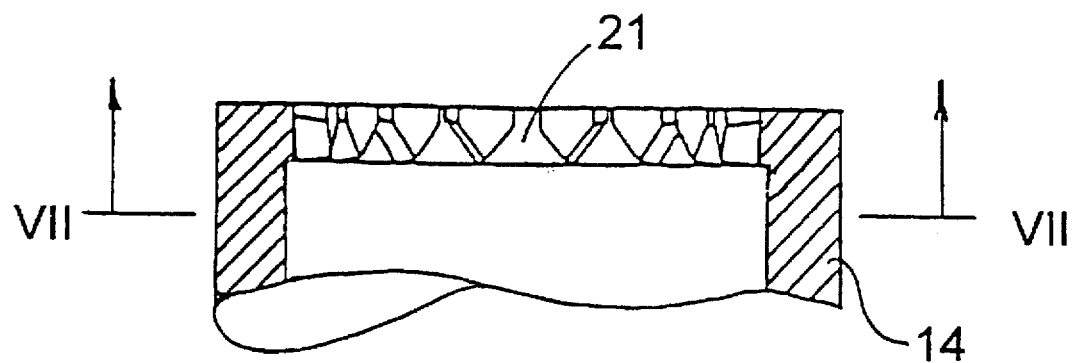
FIG. 6 is a front, sectional view of the forward end of the pen syringe.
Figure 7:
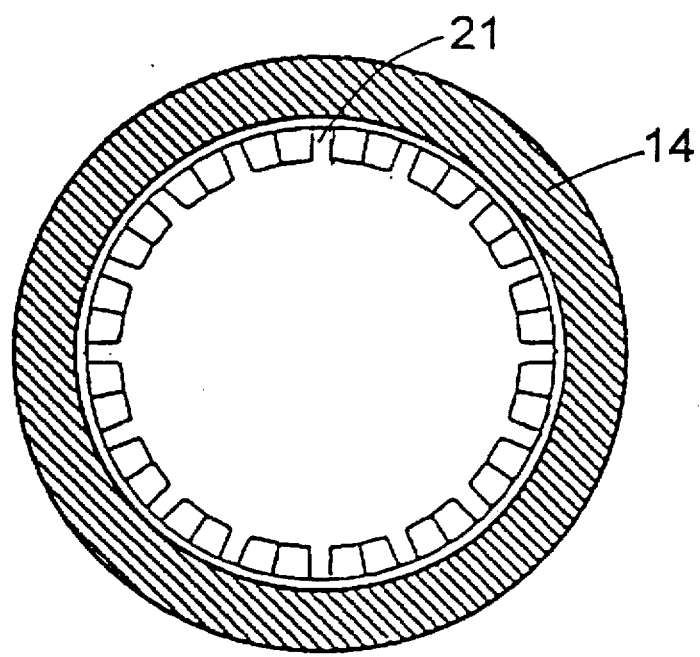
FIG. 7 is a sectional view of the pen syringe, taken in the direction of the arrows VII—VII of FIG. 6.

At its lower end the body 1 is provided with a flange 6 having triangular knobs 7 intended for cooperation with the syringe using an ampoule carrying this top. The engagement between the knobs 7 and corresponding recesses 21 (see FIGS. 4 and 6–7) in the syringe keeps the top unrotable during screwing on the needle hub.

The outer cylindric contour of the body is shown with opposite flat cuts removing the thread 5 on opposite sides of the cylinder. Such cuts in the cylindric body shape may be made to provide a key for cooperation with a specific syringe, but is in the shown embodiment made for pure moulding related reasons.

Figure 2:
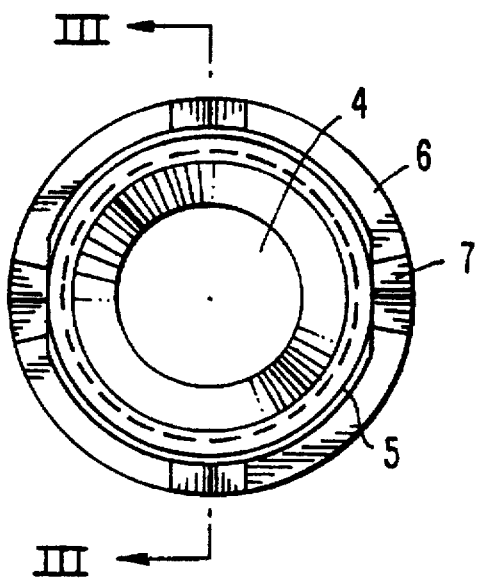
FIG. 2 shows a plan view of the embodiment shown in FIG. 1.
Figure 3:
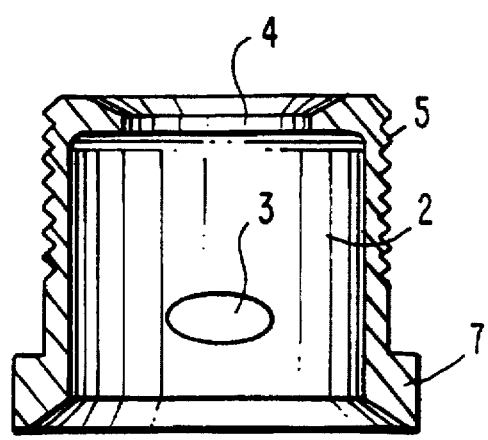
FIG. 3 shows a sectional view along the line III—III in FIG. 2.
Figure 4:
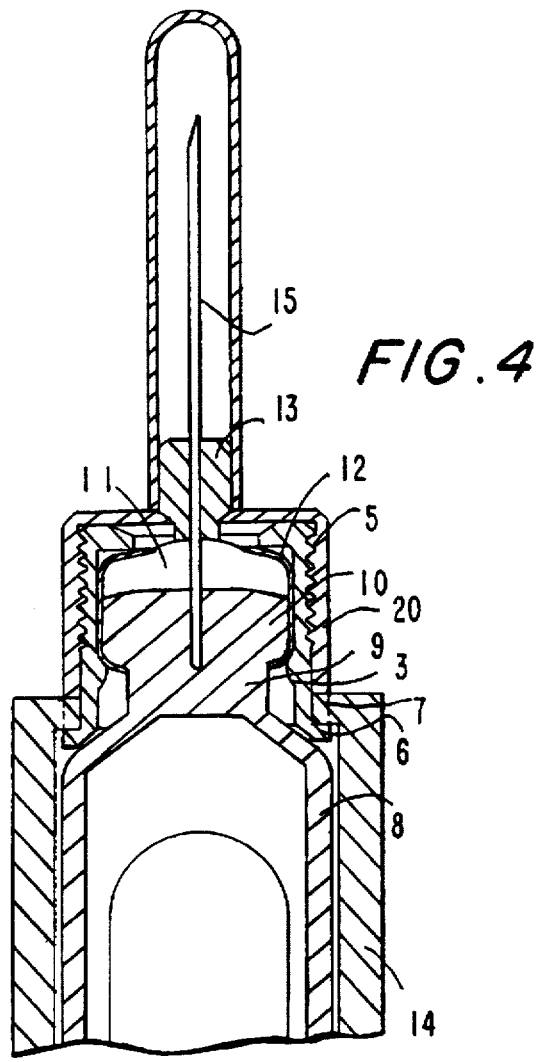
FIG. 4 shows a cylinder ampoule with an adaptor top as illustrated in FIGS. 1–3 mounted in a pen syringe.

FIG. 4 shows schematically the relevant parts of the syringe with an ampoule mounted using an adaptor top according to the invention. The parts of the adaptor top are given the reference numbers of similar parts in the embodiment shown in FIGS. 1–3. A standard ampoule 8 has a neck 9 with a flange 10 against which a rubber membrane 11 is sealingly secured by a metal cap 12 beaded under the flange 10. The bottom of the cup shaped cap 12 has an opening up through which part of the membrane 11 protrudes. The adaptor top is passed with its bore over the cap 12 and pressed down to make the protrusion 3 pass the metal cap and grip under the lower beaded edge of this cap. A needle hub 13 has a depending tubular skirt 20 having an internal thread to be screwed onto the outer thread 5 of the adaptor top with its needle 15 piercing the membrane 11 and projecting into the opening of the neck part of the ampoule. From the drawing it is noticed that the adaptor top is not the type having three protrusions 120° displaced, but has oppositely placed protrusions 3.

The ampoule 8 with the adaptor top is inserted in a syringe housing 14 from the rear end thereof with the adaptor top projecting through an end wall of the syringe housing 14 and with the flange 6 of the adaptor top abutting this end wall. The end wall has recesses 21 to be engaged by the knobs 7 on the flange 6 and the top is this way held unrotably so that the needle hub may be screwed on the top. When screwed on the top the needle hub may be tightened to clamp the end wall of the housing 14 between the flange 6 and the lower edge of the skirt 20. In another not shown embodiment the flange 6 may be omitted and the knobs 7 may be provided on the outer wall of the top and may be received in triangular recesses in the end wall of the syringe housing 14.

In this way the ampoule is held in the syringe in a way making it easy to take out an empty ampoule by unscrewing the needle hub 7 as the ampoule is not wedged in the housing.

Figure 5:
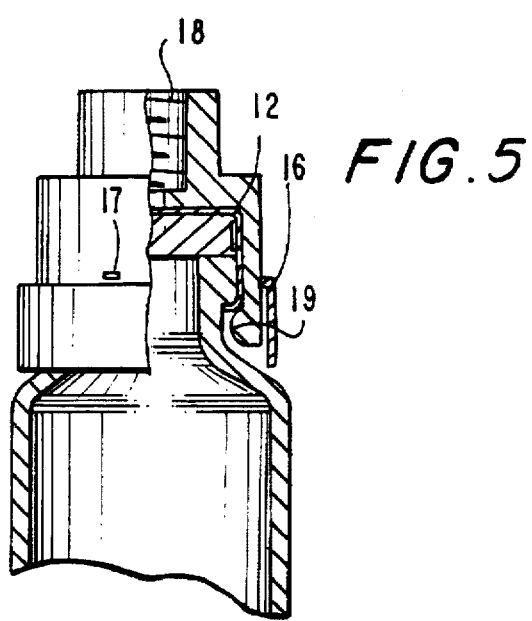
FIG. 5 shows another embodiment of an adaptor top according to the invention.

FIG. 5 shows another embodiment of an adaptor top mounted on a standard ampoule. Instead of discrete protrusions a ring-shaped protrusion 19 is running at the inner side of the bore. To make it possible to press this top over the metal cap 12 the lower edge carrying the protrusion has either to be very resilient or even to be slotted to enable a deformation allowing the protrusion to pass over the metal cap of the ampoule. Thereby the adaptor top may be too easy to remove unless as shown it is provided with an unresilient locking ring 16 which is kept in position by locking fingers 17. This adaptor top is shown having in its opening an inner thread 18 for receiving a needle hub having an outer thread.

We claim:
1. A pen syringe assembly comprising:
   (a) a housing having (i) an inner space and (ii) housing interlocking means which faces the inner space,
   (b) an exchangeable standard cartridge, having a neck part with a flange, which is closed by a rubber membrane secured against the flange by a metal cover having an edge beaded behind the flange, and
   (c) an adaptor top having (i) a bore with a diameter conforming to the outer diameter of the metal cover of the cartridge for receiving the metal cover of the cartridge therein, (ii) top interlocking means mating the housing interlocking means, and (iii) connecting means adapted to receive an exchangeable needle hub carrying a needle, wherein the adaptor top is mounted on the cartridge which has its neck part pressed into the bore, and wherein the cartridge with the adaptor top is accommodated in the inner space of the housing with the top interlocking means engaging the housing interlocking means.

2. A syringe assembly according to claim 1, wherein the adaptor top is plastic and is provided with a thread coaxial with the bore for receiving a threaded needle hub.

3. A syringe assembly according to claim 2, wherein the housing interlocking means and the adaptor top interlocking means prevent relative rotation between the syringe housing and the adaptor top.

4. A syringe assembly according to claim 3, further comprising a needle assembly comprising a needle hub having a bore with an internal thread, wherein a portion of the adaptor top projects out of a forward end wall of the housing, wherein the adaptor top thread is an exterior thread on such portion, and wherein the needle hub screws over the portion of the adaptor top having the exterior thread to clamp the end wall between the needle hub and part of the adaptor top.

5. A syringe assembly according to claim 1, wherein the bore of the adaptor top includes means for securing the metal cover against axial movement within the bore.

6. A syringe assembly according to claim 5, wherein the means for securing the metal cover within the bore comprise means to engage the metal cover after the metal cover has been inserted a predetermined distance into the bore.

7. A syringe assembly according to claim 6, wherein the means for securing the metal cover against axial movement within the bore comprises at least one protrusion in the bore that grips behind the beaded edge of the metal cover.

8. A syringe assembly according to claim 7, wherein the means for securing the metal cover against axial movement within the bore includes a locking ring.

9. A syringe assembly according to claim 1, wherein the adaptor top interlocking means are knobs at an end of the top, which knobs have triangular cross sections with the apex of the triangle directed towards an end wall of the housing, and wherein the housing interlocking means comprise corresponding triangular depressions in the housing.

10. A syringe assembly according to claim 1, wherein the top is made from a colored plastic to carry information about the content of the cartridge.

11. A syringe assembly according to claim 1, further including a needle assembly engaging the connecting means of the adaptor top.

12. A syringe assembly according to claim 1, wherein the housing interlocking means are located at an end wall of the housing.

13. In combination, an exchangeable standard cartridge, having a neck part with a flange, which is closed by a rubber membrane secured against the flange by a metal cover having an edge beaded behind the flange, and an adaptor top having:

a first, axially extending portion having a bore with a diameter conforming to the outer diameter of the metal cover of the cartridge, and an opening for exposing at least a part of the rubber membrane, wherein the metal cover is secured against axial movement within the bore;

a flange portion extending outwardly from the first portion, wherein the first, axially extending portion is adapted to pass through a forward opening in the housing of a syringe, and the flange portion is adapted to secure the adaptor top at a predetermined axial position relative to such syringe housing;

an interlocking member on the flange adapted to fit together with an interlocking means inside a syringe housing; and connecting means adapted to receive an exchangeable needle hub carrying a needle.

14. The combination of claim 13, wherein the outside surface of the first portion is at least generally circular in cross-section, wherein the flange is an annular flange, and wherein the interlocking member is a projection.

15. The combination of claim 14, wherein the projection is a knob having a triangular cross-section, in which the apex of the triangle faces the direction in which the adaptor top is intended to be passed through a syringe housing.

16. A method of supplying a first medicament and a second medicament, comprising the steps of:

(a) providing the first medicament in a first, exchangeable standard cartridge, such standard cartridge being of the type which has a neck part with a flange closed by a rubber membrane secured against the flange by a metal cover having an edge beaded behind the flange, and which is designed to be inserted into a syringe housing for dispensing the medicament through a needle;

(b) providing the second medicament in a second exchangeable standard cartridge;

(c) providing the first cartridge with a first adaptor top and providing the second cartridge with a second adaptor top, wherein each adaptor top has (i) a bore with a diameter conforming to the outer diameter of the metal cover of the cartridge and means for securing the metal cover against axial movement within the bore, and (ii) top interlocking means adapted to mate with an interlocking means in a syringe housing, wherein the interlocking means of the first adaptor top differs from the interlocking means of the second adaptor top such that a syringe having housing interlocking means that mate with the interlocking means of the first adaptor top would not accept the interlocking means of the second adaptor top; wherein the first and second adaptor tops are mounted on the first and second cartridges, with their neck parts pressed into the bore, thereby to form first and second cartridge assemblies, respectively, and wherein each cartridge assembly includes a connecting means adapted to receive an exchangeable needle hub carrying a needle; and (d) supply both the first and said second cartridge assemblies for marketing for administration to patients, wherein persons who utilize a syringe that accepts the adaptor top of said first cartridge assembly, for administering the first medicament, are unable to use the second cartridge assembly, and thereby administer the second medicament, using such syringe, thereby preventing an accidental administration of the second medicament.

17. A method according to claim 16, wherein the needle hub connecting means are provided on the respective adaptor tops, and further comprising the step of attaching an exchangeable needle hub on the connecting means.

18. A method of supplying a first medicament and a second medicament, comprising the steps of:

(a) providing the first medicament in a first, exchangeable standard cartridge, such standard cartridge being of the type having a neck part with a flange, which is closed by a rubber membrane secured against the flange by a metal cover having an edge beaded behind the flange, and designed to be inserted into a syringe housing for dispensing the medicament through a needle;

(b) providing the second medicament in a second exchangeable standard cartridge;

(c) providing the first cartridge with a first adaptor top and providing the second cartridge with a second adaptor top, wherein each adaptor top has a bore with a diameter conforming to the outer diameter of the metal cover of the cartridge and means for securing the metal cover against axial movement within the bore, wherein the first adaptor top has a color which differs from the second adaptor top so as to carry information as to the contents of each cartridge; wherein the respective adaptor top is mounted on a cartridge which has its neck part pressed into the bore, thereby forming first and second cartridge assemblies, respectively, and wherein each cartridge assembly includes a connecting means adapted to receive an exchangeable needle hub carrying a needle; and (e) supplying both the first and said second cartridge assemblies for marketing for administration to patients, wherein persons intending to administer one type of medicament are able to utilize the color coding on the first and second adaptor types to distinguish between the type of medicament contained in the respective cartridges.

19. A method according to claim 18, wherein the needle hub connecting means are provided on the respective adaptor tops, and further comprising the step of attaching an exchangeable needle hub on the connecting means.

* * * * *